United States Patent [19]

Kulli et al.

[11] Patent Number: 4,807,170
[45] Date of Patent: Feb. 21, 1989

[54] DRUG DOSE RATE CALCULATOR

[76] Inventors: John Kulli, 1929 Spruce, South Pasadena, Calif. 91030; Thomas M. Mitchell, 1715 La Cresita, Pasadena, Calif. 91103; Arthur E. Brown, 3130 S. Center St., Santa Ana, Calif. 92704

[21] Appl. No.: 845,929
[22] Filed: Mar. 25, 1986
[51] Int. Cl.$^4$ ............................................. G06F 15/42
[52] U.S. Cl. ............................ 364/413.01; 364/715.01; 604/30
[58] Field of Search ............. 364/715, 413; 604/30, 604/31

[56] References Cited

U.S. PATENT DOCUMENTS 4,308,866  1/1982  Jelliffe et al. ............... 364/413 X
4,676,776  6/1987  Howson .......................... 604/31
4,686,624  8/1987  Blum et al. ................... 364/413 X
4,709,331  11/1987  Barkett et al. ................ 364/413

Primary Examiner—David H. Malzahn
Attorney, Agent, or Firm—John H. Lynn

[57] ABSTRACT

A drug dosage calculation system includes a hand held, battery operated computing device for use by nurses and other clinical personnel to make calculations pertaining to the drug administration rate and the corresponding flow rate settings of IV systems that are used for intravenous administration of fluids to a patient. Flow rate setting, drug dose rate, drug amount and the amount of IV solution into which the drug is diluted are the primary variables used in such calculations. A keyboard is used to supply data to a computation device that computes the unknown quantity. A display device displays the data input to the computer and also displays data calculated for the unknown variable.

21 Claims, 18 Drawing Sheets

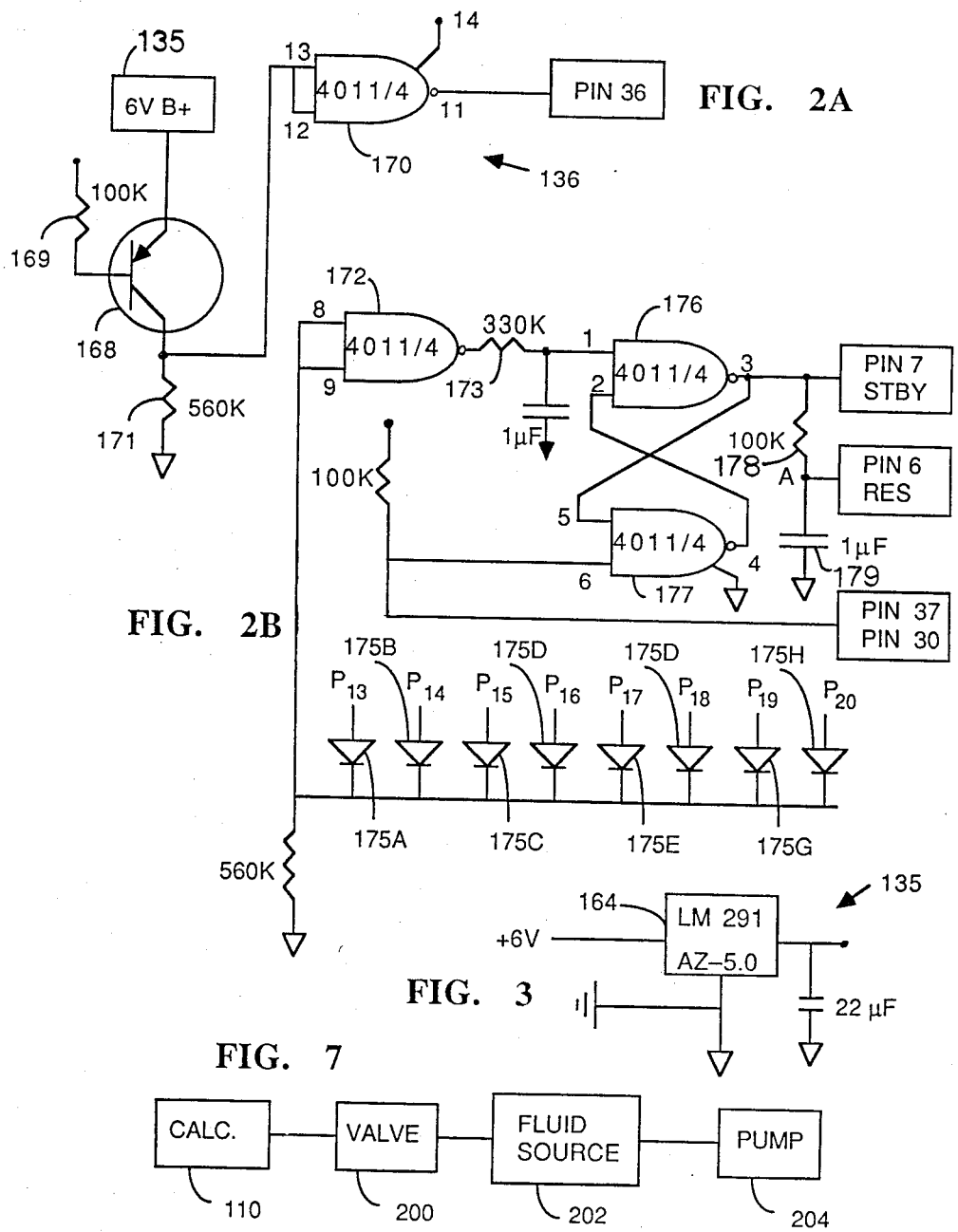

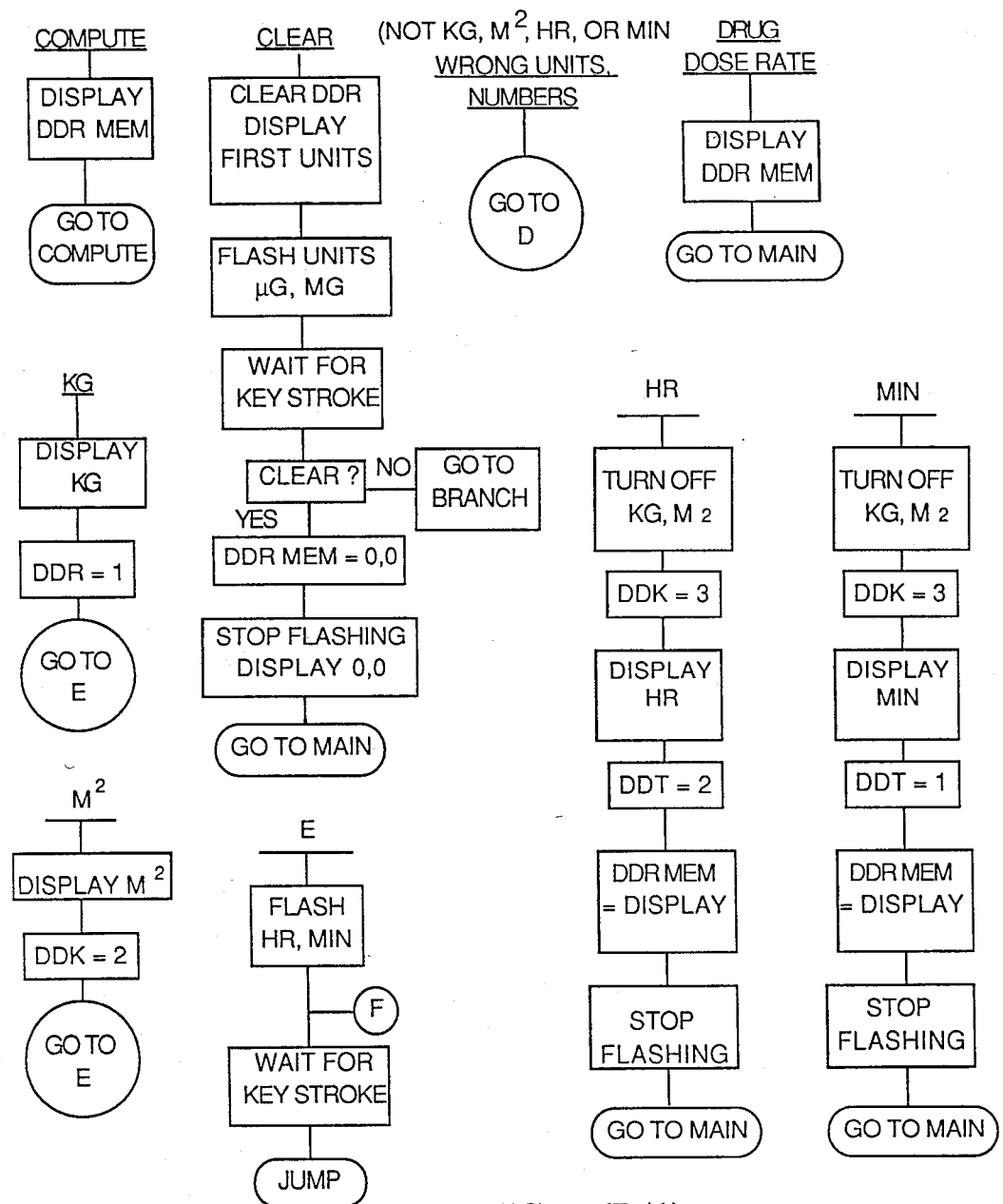
FIG. 6D(1)

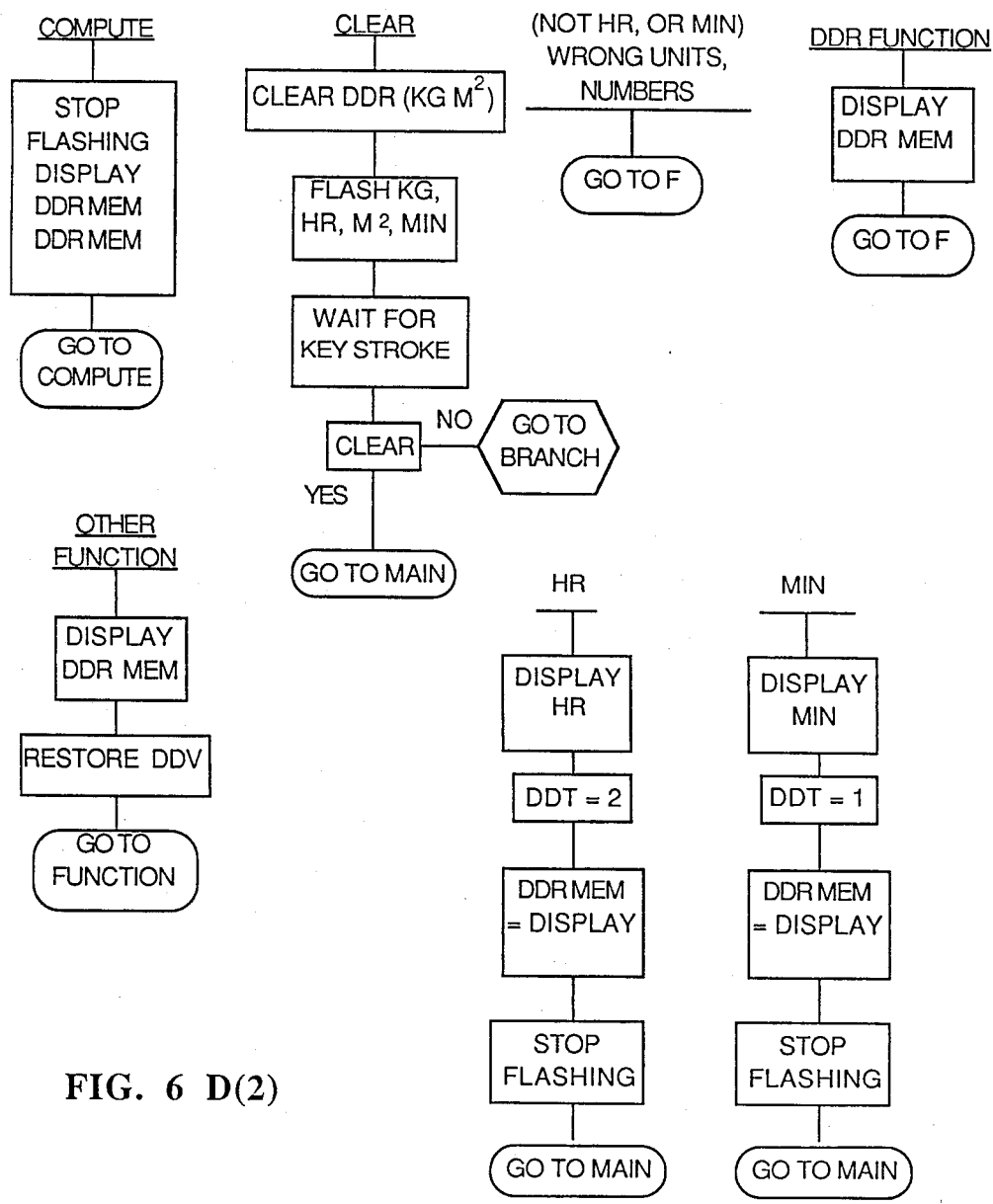
FIG. 6 D(2)

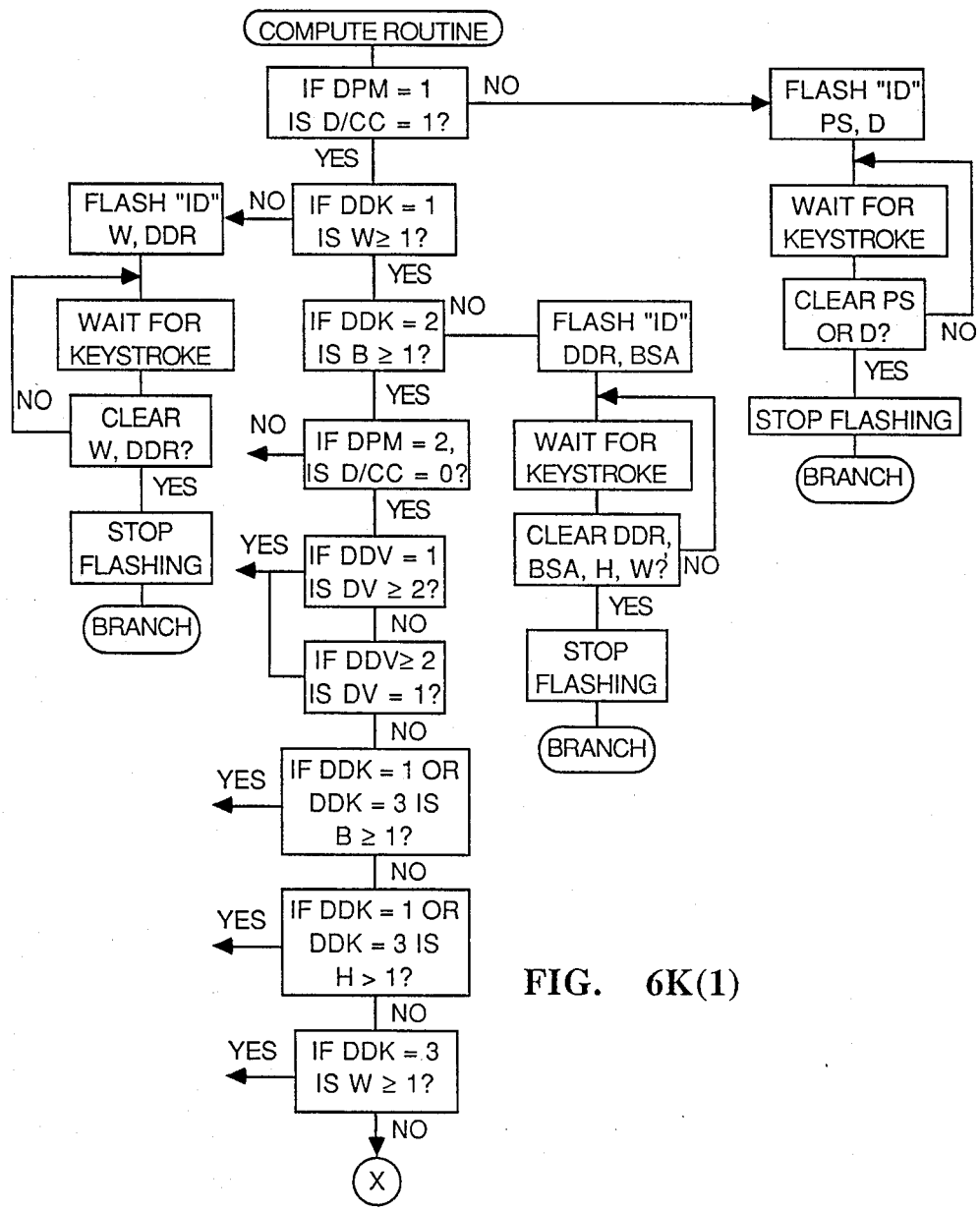
FIG. 6K(1)

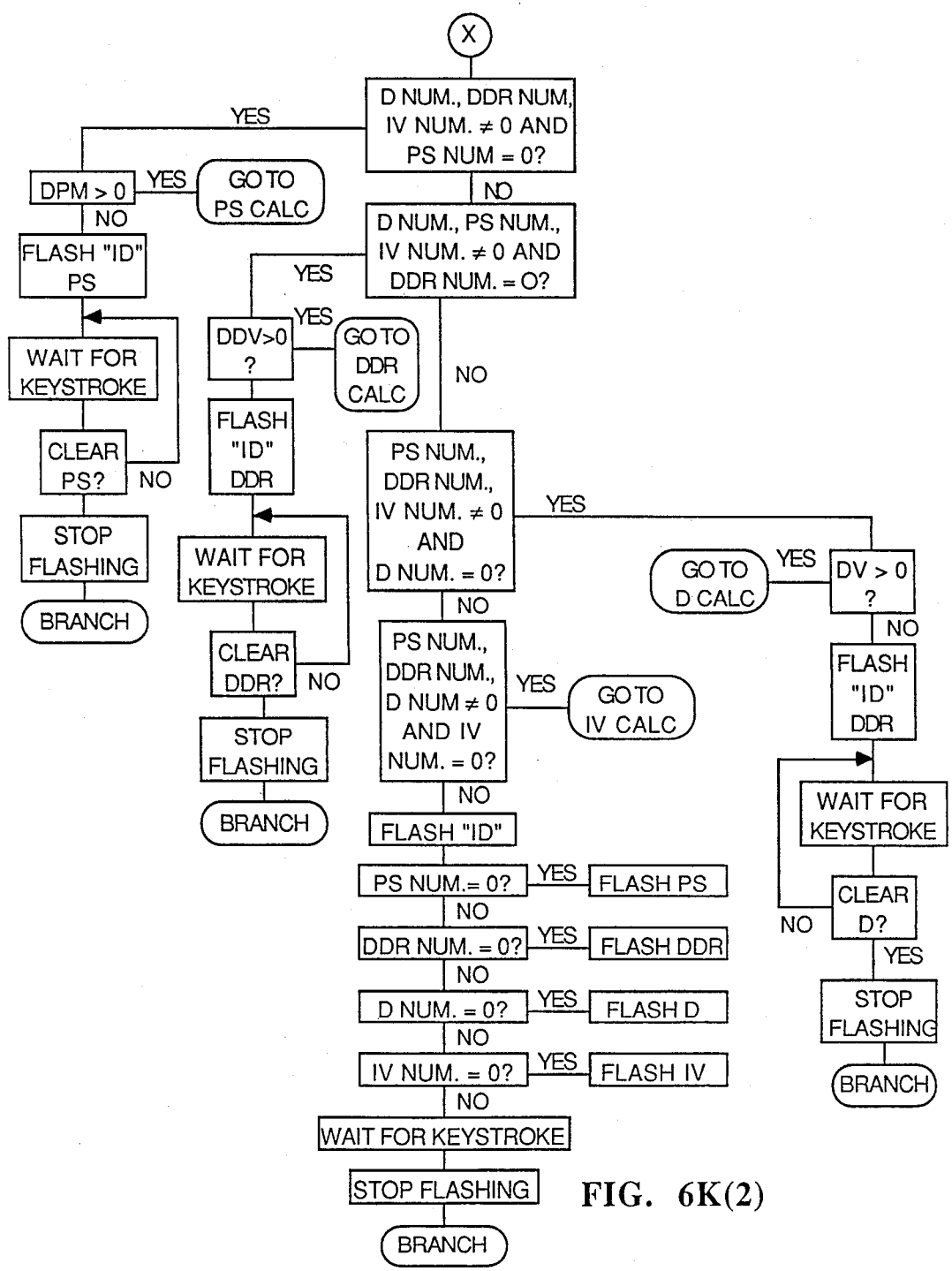
FIG. 6K(2)

DRUG DOSE RATE CALCULATOR

BACKGROUND OF THE INVENTION

This invention relates generally to apparatus and methods for administering drugs and other substances intravenously into a patient. The invention relates more particularly to apparatus and methods for assuring that a prescribed dosage is actually administered to the patient.

There are significant difficulties in assuring administration of prescribed dosages to patients. The difficulties arise from the various units in which prescriptions are given and from the units that define the dosage rates that are administered by typical intravenous equipment. Drug administration rates are commonly prescribed in milligrams, micrograms or UNITS per unit of time. A UNIT is a measure of an amount of a drug. The time is usually given in hours or minutes. The patient's body weight in kilograms or pounds may be a factor in the drug administration rate. The patient's body surface area, commonly given in square meters, may also be considered in determining the drug administration rate.

Actual drug administration rates are determined by a pump setting that is normally a certain number of drops per minute or cubic centimeters per hour. A physician will normally prescribe a drug administration rate in units of measure with which he is familiar or in units recommended by the drug's manufacturer. The nurse or other technician who actually sets the pump rate must convert the prescribed drug administration rate into an appropriate number of drops per minute or cubic centimeters per hour so that the pump may be set at a value appropriate for delivering the prescribed amount of drug to the patient.

Present methods for determining the pump rates include hand calculations and calculations using general purpose calculators. These methods are subject to error with results that are sometimes catastrophic.

Therefore, there is a need in the art for a simple, reliable device for calculating drug dose rates to facilitate administration of prescribed dosages.

SUMMARY OF THE INVENTION

The present invention provides a drug dosage calculation system and method that overcomes the deficiencies of prior systems and methods. The invention comprises a hand held, battery operated computing device for use by nurses and other clinical personnel to make calculations pertaining to the drug administration rate and the corresponding pump settings of IV pumps that are used for intravenous administration of fluids to a patient. The operational features of the computing device according to the invention are self explanatory and fail-safe so that improper dosage calculations cannot be made.

The computing device according to the invention accepts input values for three of four variables used in determining the amount of drug to be administered to the patient. These variables are pump setting, drug dose rate, drug amount and the amount of IV solution into which the drug is diluted.

A drug dosage calculation system according to the invention for calculating a variable selected from the group consisting of the pump setting, intravenous solution volume, drug dose rate and drug quantity when three of the variables are known for intravenous administration of drugs or the like to a patient by means of a pump and a catheter connected to the pump, comprises: a computation device; keyboard means for inputting data for three of the variables to the computation device; and display means for displaying the data input to the computing means and for displaying data calculated for the previously unknown variable.

The keyboard in the system of the invention includes a first set of keys connected to the computation device for supplying signals thereto indicative of the pump setting, intravenous solution volume, drug dose rate and drug quantity variables; a second set of keys connected to the computation device for supplying signals thereto indicative of the numerical value of the selected variable; and a third set of keys connected to the computation device for supplying signals thereto indicative of the units of the selected variable. The computing device may provide an output to a valve for controlling the rate of fluid flow from a source of fluid.

The method of the invention for determining one of the variables selected from the group consisting of the pump setting, intravenous solution volume, drug dose rate and drug quantity when three of the variables are known for intravenous administration of drugs or the like to a patient by means of a pump and a catheter connected to the pump, comprises the steps of: supplying data indicative of the known variables to a computation device; supplying data indicative of the numerical values of the known variables to the computation device; supplying data indicative of the units of the known variables to the computation device; supplying data indicative of selected units of the unknown variable to the computation device; and computing the previously unknown variable.

BRIEF DESCRIPTION OF THE DRAWINGS

FIGS. 2A and 2B are a schematic diagram of a power control circuit that may be included in the invention;

FIG. 3, is a circuit diagram of a regulated power supply that may be included in the invention;

FIG. 6K(2) illustrates the second half of the compute routine of the invention;

FIG. 7 is a block diagram of a drug administration system including a drug dose rate calculator connected to a valve for controlling the amount of drug to be administered to a patient.

DESCRIPTION OF THE PREFERRED EMBODIMENT

Figure 1:
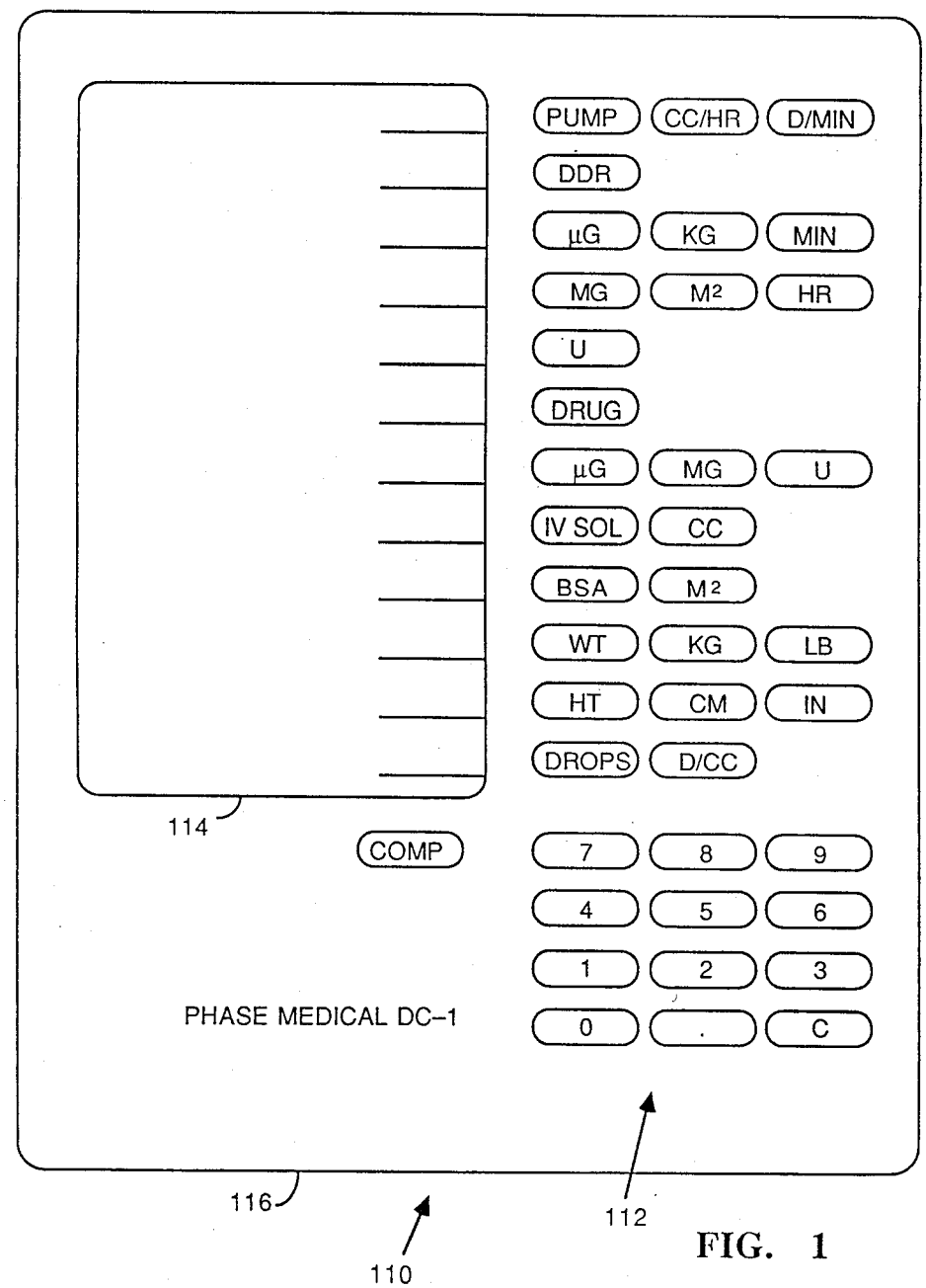
FIG. 1 illustrates a keyboard and display arrangement that may be included in the invention.

Referring to FIG. 1, a drug administration rate calculator 110 according to the invention includes a keyboard 112 and a display 114 mounted in a case 116. The keyboard 112 and the display 114 are connected to a computation system 118, shown in FIGS. 4 and 5. The display 114 is preferably a liquid crystal display well known in the art, and the keyboard 112 may be any suitable data entry device well known in the art for inputting data to electronic calculators and computers. The computation system 118 preferably comprises well-known CMOS technology so that it can operate for extended periods of time on the power available from conventional batteries (not shown).

Still referring to FIG. 1, the keyboard 112 has keys for each of the variables that are considered in intravenous administration of a drug to a patient. The drug administration rate calculator 110 permits selection of the unknown variable and its units, where there is a choice of units, so that the numerical value of the unknown may be calculated. The labeling of these variable keys and the units for the variables are summarized in TABLE I below.

TABLE 1
KEYBOARD VARIABLE AND UNIT KEYS

| Key Label | Key Variable | Units |
|---|---|---|
| PUMP | Pump Setting | cc/hr, drops/min |
| DDR | Drug Dose Rate | μg, kg, mg per hr or per min, per m² or per kg, if specified |
| DRUG | Drug Amount | μg, mg or UNITS |
| IV SOL | IV solution Volume | cc |
| BSA | Body Surface Area | m² |
| WT | Body Weight | kg, lb |
| HT | Body height | cm, inches |
| DROPS | Drops of Drug | Drops/cc |

The pump setting variable should be understood to include any means for controlling the flow of drug to a patient. For example, in some systems it is necessary to control the setting of a valve (not shown) to regulate the flow of fluid from a container above the patient. The height differential supplies the pressure necessary for the fluid to enter the patient's body so that pumping is unnecessary.

The PUMP, DDR, DRUG and IV SOL keys are the primary variables that are considered in intravenous drug administration. The remaining variables sometimes must be used to provide data necessary for determining some of the primary variables. For example, the patient's body surface area may be calculated from the empirical formula $$BSA = 0.007184 W^{0.425} H^{0.725},$$

where BSA is the body surface area, W is the patient's body weight in pounds and H is the patient's height in inches. The empirical formula for calculating the body surface area is preferably included in the software as explained subsequently.

The keyboard 112 and display 114 are preferably arranged so that LCD annunciators correspond to the keys. The annunciators indicate the units of the variables. After the drug administration rate calculator 110 is turned on, the annunciators for the four primary keys turned on. The keyboard 112 includes a number pad that has a decimal point and digit keys 0-9, a clear key C and a compute key, labeled COMP.

In order to input data for a known variable, the user first presses the key corresponding to the variable and then depresses keys to input the numerical value of the variable. The user must next depress a key to select the units for the variable if there is a choice of units available. After the input sequence is complete, the numerical value and the units of the variable last input are displayed on the LCD display 114. The variables may be input to the drug administration rate calculator 110 in any desired order. Any time a variable key is depressed, previous numerical values of that variable clear from the display 114. The display 114 then displays a flashing legend that identifies the variable; all permissible units for the variable are displayed; and all data that was completely entered with numerical values and units is maintained in a memory stack within the computational system until a new complete set of data for that variable is entered via the keyboard 112.

The primary purpose of the drug administration rate calculator 110 is to determine the pump setting value from a given drug dose rate. Occasionally it will be necessary to calculate the drug dose rate from the pump setting, and sometimes it is necessary to calculate the amount of drug or intravenous solution to be used. Calculation of the body surface area from the weight and height is a convenience feature of the drug administration rate calculator 110, but is not an essential function of the device. Body surface areas may be obtained from tables of such data for any given height and weight, rather than being computed.

The drug administration rate calculator 110 will not store values entered for all four primary variables. For example, if the operator enters data for all four variables from the keyboard, either the drug dose rate or the pump setting will clear from the display. The drug administration rate calculator 110 accepts entered values of three of the primary variables and then calculates the fourth primary variable.

The hardware included in the drug administration rate calculator 110 includes a microcomputer 130 connected to the keyboard 112 to receive inputs therefrom. The microcomputer 130 preferably includes either an Hitachi model HD63P01M1, an Hitachi HD6301 or other similar device. The microcomputer 130 provides outputs to a pair of display drivers 132 and 134 which drive the segments of the display 114. The drivers 132 and 134 are preferably Hitachi HD63602 integrated circuits or the equivalent. The microcomputer 130 and the display drivers 132 and 134 receive power from a power supply 135, shown in FIG. 3. A power control circuit 136, shown in FIG. 2 supplies a low voltage warning signal if the voltage drops below a predetermined value and turns the power supply 135 off after it has been on for a predetermined time.

Figure 4:
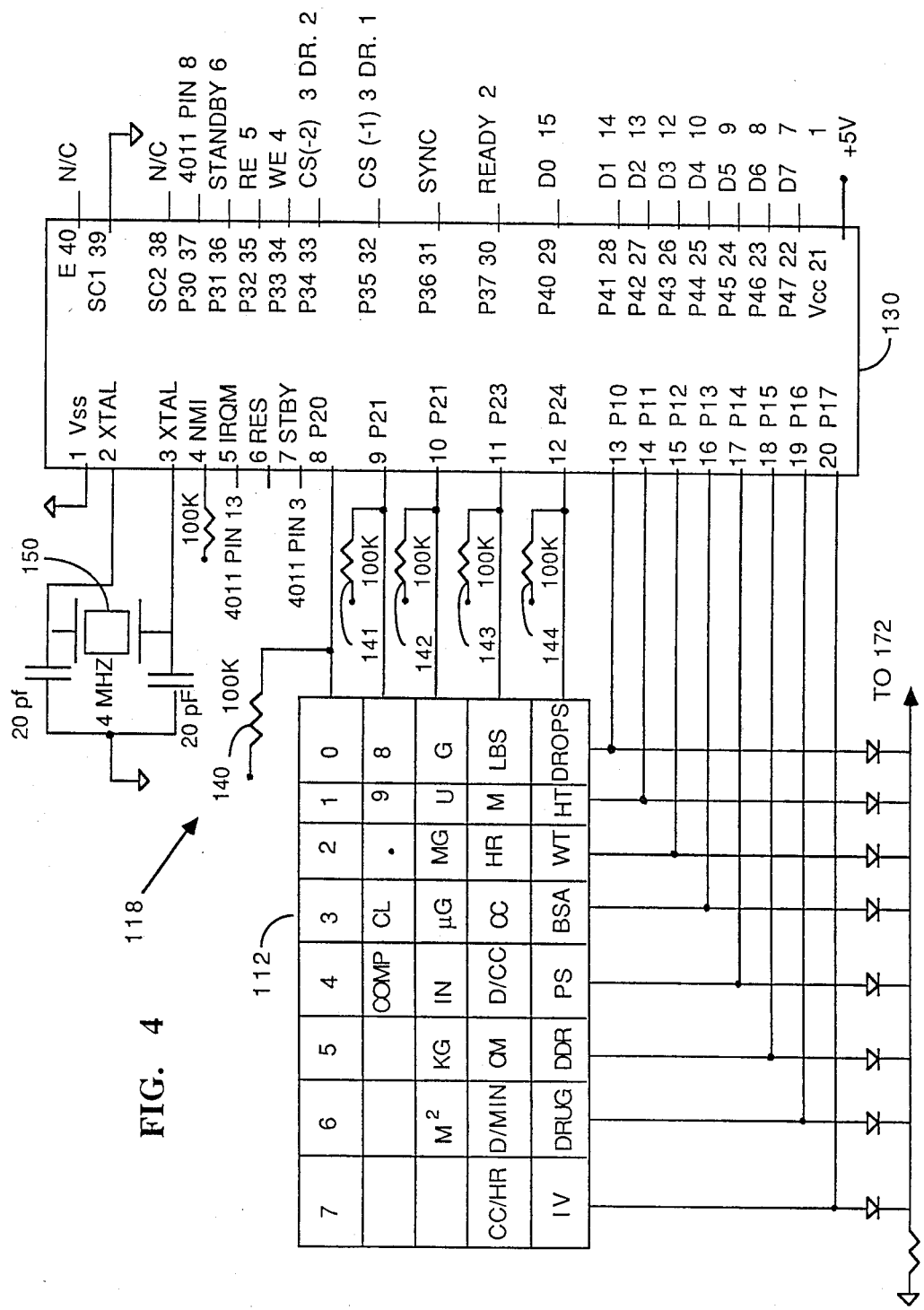
FIG. 4 illustrates connections between the keyboard of FIG. 1 and a microcomputer.
Figure 5:
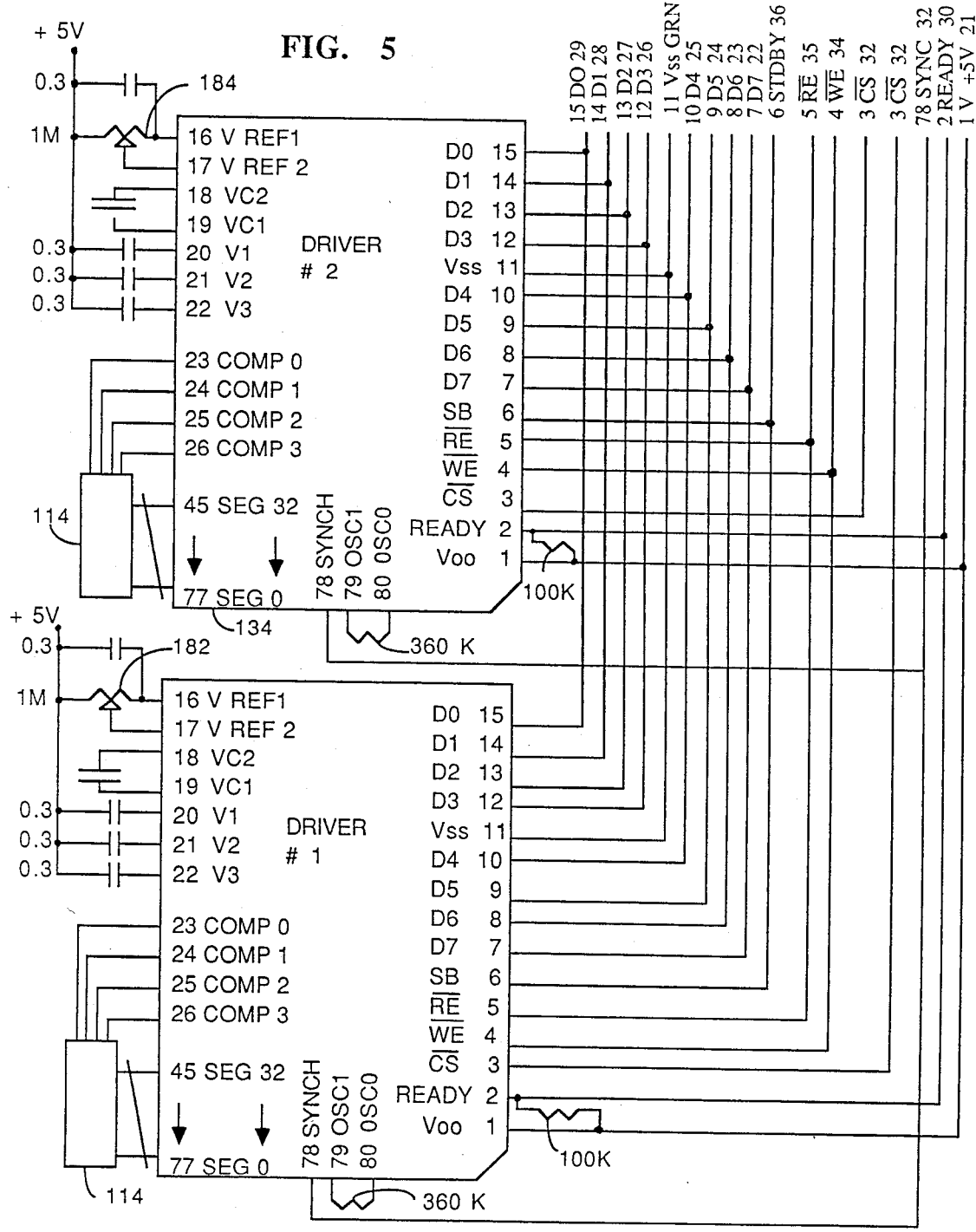
FIG. 5 illustrates a display circuit board that may be included in the invention.

As shown schematically in FIG. 4, the keyboard 112 is a 5×8 matrix. The elements of the matrix include the variables of TABLE I, the units of the variables, the numeric keypad and the compute key. In the exemplary embodiment of FIG. 4, the eight columns of the keyboard 112 are input to port 1 of the microcomputer 130. Port 1 includes the pins 13-20 of the microcomputer 130. Each of the pins represents a bit of the signal sent between the microcomputer 130 and the keyboard 112. For example, pin 13 corresponds to port 1, bit 0; pin 14 corresponds to port 1, bit 1, etc. The five rows of the keyboard 112 are connected to port 2 of the microcomputer 130. Port 2 includes pins 8-12. Pin 8 corresponds to port 2, bit 0; pin 9 corresponds to port 2, bit 1, etc.

The keyboard 112 addresses the microcomputer 130 by providing low signals on the lines which intersect in the matrix. For example, depression of the key corresponding to the patient's body weight, provides low signals to port 1, bit 2 and port 2, bit 4 of the microcomputer 130. The WT light of the keyboard 112 then lights up. If the user then depresses the key to indicate that the units of the patient's height are inches, the microcomputer 130 receives low signals at port 1, bit 4 and port 2, bit 2 to light up the IN light on the keyboard 112. Resistors 140-144 are connected to pins 8-12, respectively, to bring unaddressed lines between port 2 and the keyboard 112 to logic high states.

The microcomputer 130 includes a first group of pins numbered 1-20 and second group of pins numbered 30-40. The pins 8-12 and 13-20 form the first and second output ports previously described. Pin 1 is connected to ground. Pins 2 and 3 are connected across a crystal oscillator 150, which supplies 4 MHz clock signals to the microcomputer 130. Pin 4 is a non-maskable interrupt input not used in the present invention and therefore tied high by a 100 KΩ resistor 162. Pin 5 is an interrupt request input that receives a signal warning of low power supply voltage. Pin 6 is a reset input for reapplying power to the microcomputer 130 after an interruption. Pin 7 is a standby input that receives a signal for placing the microcomputer 130 in a standby mode to conserve power.

The second group of pins includes an eight bit output port 3 that has bits numbered $P_{30}$ through $P_{37}$, where $P_{30}$ means port 3, bit 0. Port 3, bit 0 is connected to port 2, bit 0 to activate the keyboard 112 after the drug administration rate calculator 110 has been turned on or reset. Port 3, bit 1 is outputs a signal for initiating the standby mode. Port 3, bit 4 and port 3, bit 5 are chip select outputs for selecting which of the two display drivers 132 and 134 will receive data from the microcomputer 130. Port 3, bit 6 outputs a signal indicating that the microcomputer 130 is ready to accept inputs from the keyboard 112. The second group of pins further includes an eight bit output port 4 that has bits numbered $P_{40}$ through $P_{47}$ that supply data to the display drivers 132 and 134.

Referring to FIG. 3, the power supply 135 that preferably includes a low drop out voltage regulator 164 such as a National Semiconductor model LM 2931. The voltage regulator 164 receives voltage from any convenient source, such as a combination of batteries that outputs about 7.5 volts. The voltage regulator 164 preferably regulates the voltage down to 5.2 volt and provides an output of about 5.0 volts between an output terminal and ground. The output voltage may be taken across a capacitor 165, which preferably has a capacitance of about 22 μF.

The drug administration rate calculator 110 preferably includes the power control circuit 136 of FIG. 2A for controlling application of power to the microcomputer 130. The power control circuit 136 includes a transistor 168 having its base connected to receive the output of the power supply 135 through a resistor 169, which preferably has a resistance of about 100 KΩ. The emitter of the transistor 168 is connected to a 6 volt $V_{cc}$ source. The collector is grounded through a resistor 171 of about 560 KΩ.

The collector is also connected to a 100 kΩ resistor, which is connected to input pins 12 and 13 of a NAND gate 170. Pin 13 of the NAND gate 170 is connected to input pin 5 of the microcomputer 130. When the voltage from collector to base of the transistor 168 drops to about 0.7 volt, the transistor 168 turns off and provides a low signal to input pin 5 of the microcomputer 130, which then turns off. An output pin 11 of the NAND gate 170 is connected to pin 36 of the microcomputer 130 to control entry of the microcomputer 130 into a standby mode.

Referring to FIG. 2B, a second NAND gate 172 has input terminals 8 and 9 connected to ground through a resistor 171, which is preferably about 560 KΩ. The input terminals 8 and 9 are also connected to the anodes of a plurality of diodes 175A-175H, which have their anodes connected to eight columns of the display 112 as shown in FIG. 4.

The NAND gate 172 provides an output through a resistance 173 of about 330 kΩ to an input terminal 1 of a flip flop 174 formed of a pair of NAND gates 176 and 177 connected as an RS latch. An input 6 of the NAND gate 177 is connected to inputs 8 and 9 of the NAND gate 172, which also receive inputs from pin 37 of the microcomputer 130. An output 3 of the NAND gate 176 is connected to an input 5 of the NAND gate 177, and an output 4 of the NAND gate 177 is connected to an input 2 of the NAND gate 176. The inputs of the flip flop are normally high and must be pulsed to zero to change the state of the flip flop outputs. The output of the flip flop 174 is taken at pin 3 of the NAND gate 176 and is connected to input pin 7 of the microcomputer 130. The output of the flip flop 174 is also connected to input pin 6 of the microcomputer 130 through a resistor 178 of about 100 KΩ. The junction of the resistor 178 and pin 6 of the microcomputer 130 is grounded through a capacitor 179 of about 1.0 μF.

If the power supply 135 is providing adequate power so that the transistor 168 is conducting, the microcomputer 130 is on and outputs a signal to input pin 8 of the NAND gate to indicate that the drug administration rate calculator 110 is ready for operation. After the drug administration rate calculator 110 has been on for a predetermined time, such as twenty seconds, the output of the NAND gate, which is connected to the standby input of the microcomputer, goes low. The microcomputer 130 then goes into a standby mode until it is reset.

Each of the drivers 132 and 134 is capable of driving 208 segments of the display 114. A segment is any portion of the LCD display array that lights up at one time in response to a single signal from one of the drivers 132 and 134. Each numeral of the display 114 is seven segments. The letters indicating the drug dose rate are one segment. Two drivers are required because the display 114 has more than 104 segments. The drivers 132 and 134 are each separate computers that store and output data. The drivers 132 and 134 get data from the microcomputer 130 and output the last information received. The drivers 132 and 134 update the display 114 at a rate of 130 times per second, which provides convenient reading of the display 114.

The voltages output from the drivers 132 and 134 to the display 114 may be adjusted by adjusting the resistance of trimmer resistors 182 and 184 connected between the power supply 135 and the power input pins of the drivers 132 and 134 respectively. The display 114 is preferably a multiplex LCD display, which is well-known in the art. Four different common lines connected to pins 23-26 of the drivers 132 and 134 drive the display 114 in a time domain.

Port 4 of the microcomputer 130 outputs data to the driver selected by means of one of the chip select lines in port 3 described above. Except for the chip select lines, the connections between the drivers 132 and 134 and the microcomputer are identical. Port 3 provides reset, standby, ready and clock signals to the driver whose chip select line has been brought low by the microcomputer 130.

Figure 6A:
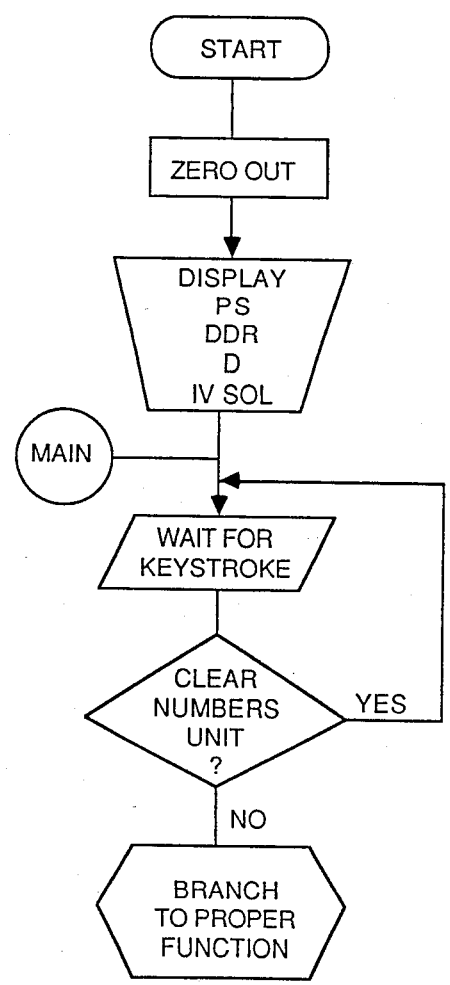
FIG. 6A illustrates a flow chart of start-up routine of the invention.

Operation of the drug administration rate calculator 110 is initiated by turning on the start switch 180 to start the sequence of steps shown in FIG. 6A. All of the display 114, the lights for the pump setting, the drug dose rate, drug and IV solution are turned on at the beginning of the sequence. The drug administration rate calculator 110 then waits for a keystroke to select one of the variables PS, DDR, D, IV SOL, DROPS, the body weight or the body height. The variables may be entered in any order. Variable selection should be done at the next keystroke.

Referring to FIG. 7, the drug administration rate calculator 110 may be connected to a valve 200, which is preferably an electrically controlled solenoid valve. The valve 200 is in fluid communication with a source 202 of pressurized fluid to regulate the flow of the pressurized fluid to the patient. The fluid may be pressurized by a pump 204 or it may be pressurized by a height differential between the fluid source and the point of insertion of the IV tube into the patient.

Pump Setting Routine

Figure 6B:
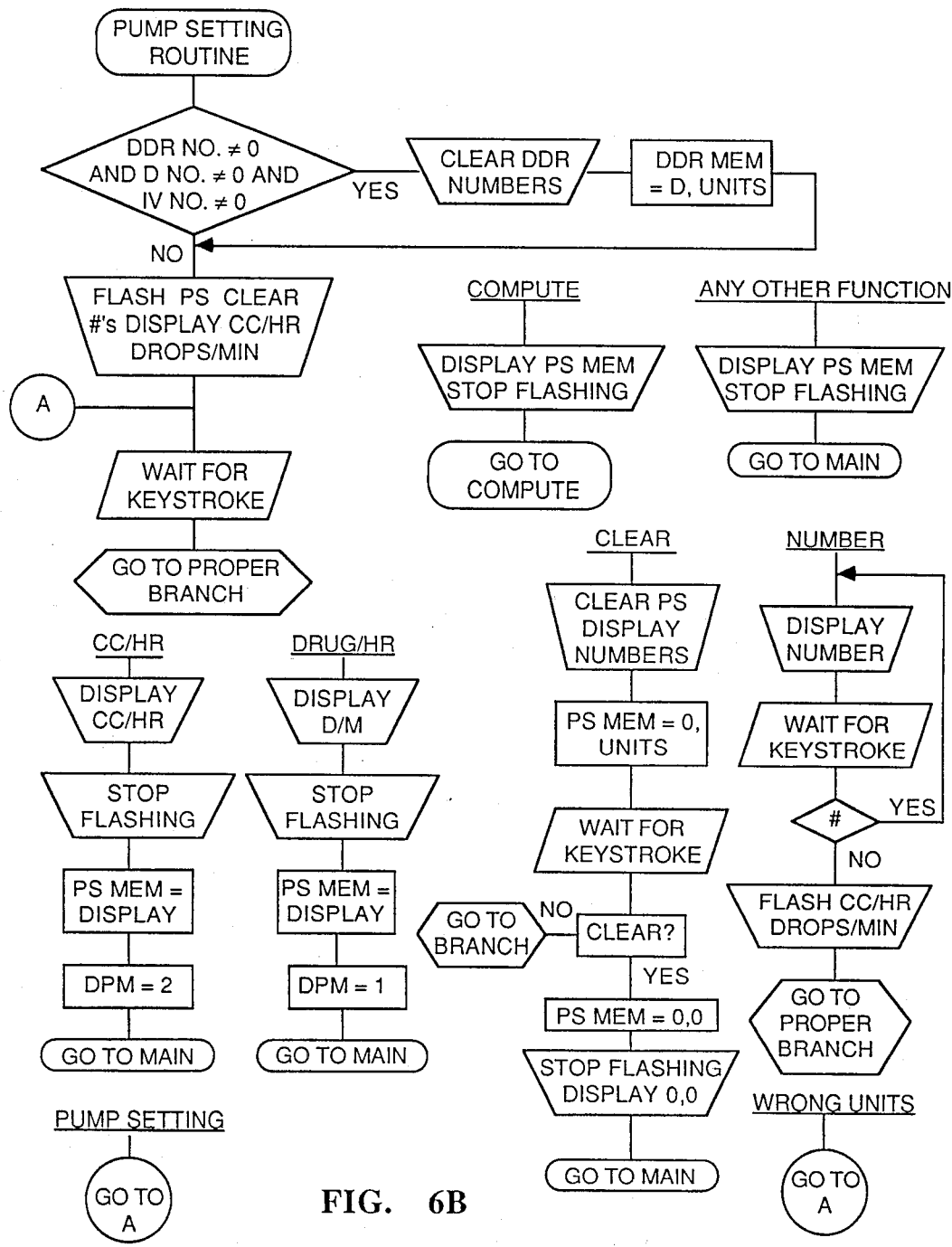
FIG. 6B illustrates a flow chart of the pump setting subroutine of the invention.

If the operator depresses the pump setting key, the drug administration rate calculator 110 enters the routine shown in FIG. 6B. The PS light flashes and the cc/hr and drops/min segments of the display 114 are lighted. After a key is depressed, the microcomputer compares the D, DDR and IV SOL numbers to zero. If all these numbers are nonzero, the DDR numbers are cleared from the memory and from the display 114. The units of the DDR are maintained. The drug administration rate calculator 110 then waits for a keystroke, which causes the microcomputer 130 to jump to the compute, cc/hr, drop/min, clear, number, pump setting, wrong units or any other function sequences shown in the lower half of FIG. 6B.

If the next keystroke is the compute command, the pump setting number from the memory is displayed and the microcomputer 130 goes to a compute routine described subsequently with reference to FIG. 6K.

If the cc/hr key is depressed, the cc/hr segments of the display 114 light up and the PS light stops flashing. The pump set segments of the display 114 are lighted, and then the microcomputer goes to the main sequence of FIG. 6A and awaits a keystroke, which ordinarily will be a number.

If the key for drops/min is depressed, then the corresponding portion of the display 114 is lighted. The pump setting light stops flashing and the pump setting from the memory is displayed. The microcomputer goes to the main sequence of FIG. A and awaits a keystroke, which ordinarily will be a number.

If the operator wishes to abort the sequence, the clear key is depressed, which causes all numbers and units to clear from the display 114. The drug administration rate calculator 110 then awaits a keystroke indicating further instructions.

If a number key is depressed, the segments of the display 114 corresponding to the number are lighted and the cc/hr and drops/min units are flashed to indicate that the available choices for the units of pump setting. After selection of units for pump setting, the process goes to another branch of the sequence described subsequently. If keys for the wrong units or for the pump setting are depressed, the program goes to point A of the pump setting routine and awaits a keystroke.

If the key for any other function not described above was depressed the program goes to the corresponding routine.

Drug Dose Rate Routine

Figure 6C:
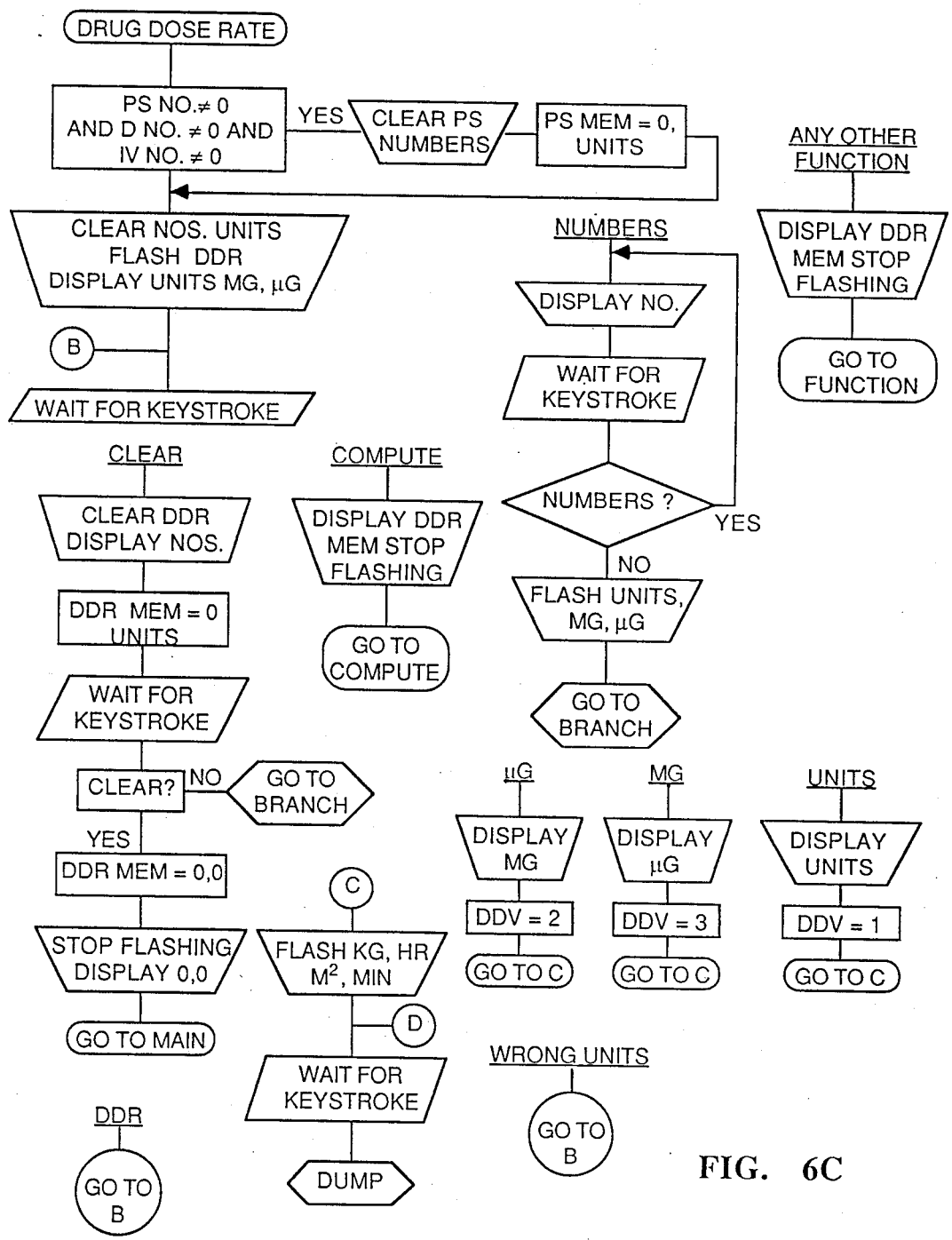
FIG. 6C illustrates the first half of the flow chart of the drug dose rate subroutine of the invention.

If the operator selects the drug dose rate from the main sequence of FIG. 6A, the microprocessor 130 goes to the drug dose rate routine shown in FIG. 6C. After a key is depressed, the microcomputer compares the D, PS and IV SOL numbers to zero. If any of the numbers are not zero, then the microcomputer 130 clears the PS numbers and flashes the PS light. The drug administration rate calculator 110 then awaits a keystroke, which will cause the microcomputer 130 to jump to either the clear, compute, numbers, micrograms, milligrams, units or any other function sequences shown in the lower half of FIG. 6C.

Depression of the clear key causes the microcomputer 130 to return to the main sequence of FIG. 6A to await another keystroke.

Depression of the compute key causes the number for the drug dose rate from memory to be displayed and the DDR light to stop flashing and causes the microcomputer 130 to go to the compute routine.

Depression of any other function key causes the microcomputer 130 to go to the routine for the selected function.

Depression of a number key causes the segments of the display 114 corresponding to the number to light up. The drug administration rate calculator 110 then awaits another keystroke. If another number key is depressed, the number is displayed and the drug administration rate calculator 110 again awaits another keystroke. After the numbers are entered, the milligram, microgram and UNITS lights are flashed to indicate the possible units for the drug dose rate. The selected unit is displayed, and then the microcomputer 130 goes to part C of the drug dose rate routine shown in the lower right corner of FIG. 6C The lights for kilograms, hours, square meters and minutes are flashed so that the user can enter data related to the weight or body surface area of the patient and the selected time units.

If the wrong units or the DDR keys are depressed, the microcomputer 130 goes to point B of the DDR routine and awaits a keystroke.

Referring to FIG. 6D, if the KG key are depressed as one of the units of the drug dose rate, then KG is displayed and the program continues to the sequence E of FIG. 6D. The display segments of HR and MIN flash, and the drug administration rate calculator 110 awaits a keystroke to select the time unit before jumping to the compute, clear, wrong units, DDR, other function, HR or MIN sequences shown in the lower portion of FIG. 6D.

If the $M^2$ key is depressed, $M^2$ is displayed and sequence E is repeated.

If the HR key is depressed, KG and $M^2$ are turned off and HR is displayed. The drug dose rate from the memory is displayed and the microcomputer returns to the main sequence.

If the MIN key is depressed, KG and $M^2$ are turned off and MIN is displayed. The drug dose rate from the memory is displayed and the microcomputer returns to the main sequence.

Drug Routine

Figure 6E:
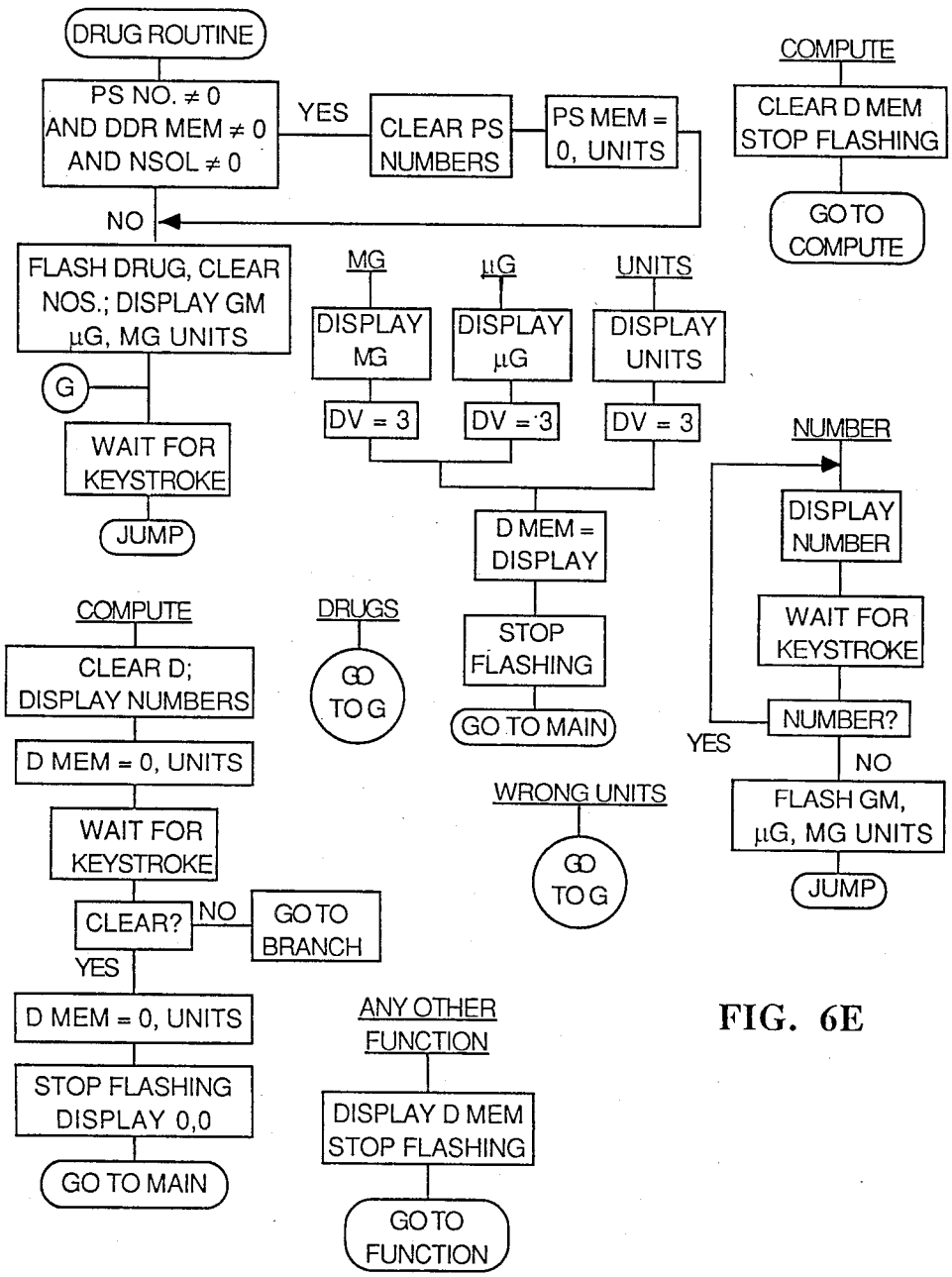
FIG. 6E illustrates the flow chart for the drug subroutine of the invention.

Depression of the drug key in the main sequence causes the microcomputer 130 to enter the drug routine shown in FIG. 6E. After a key is depressed, the microcomputer compares the D, PS and IV SOL numbers to zero. If any of the numbers are not zero, then the microcomputer 130 clears the PS numbers and flashes the PS light. The drug administration rate calculator 110 then awaits a keystroke to select one of the computer, number, milligrams, micrograms, UNITS or any other function sequences shown in the lower portion of FIG. 6E.

The compute and any other function sequences for the drug routine are the same as for the routines described previously.

Depression of the number keys for the drug amount causes the gram, microgram, milligram and UNITS keys to flash, and causes the microcomputer 130 to jump to one of the sequences for displaying the selected unit for the drug amount.

If any of the keys for selecting units for the drug amount are depressed, the selected unit is displayed before the microcomputer 130 returns to the main sequence of FIG. 6A.

IV Routine

Figure 6F:
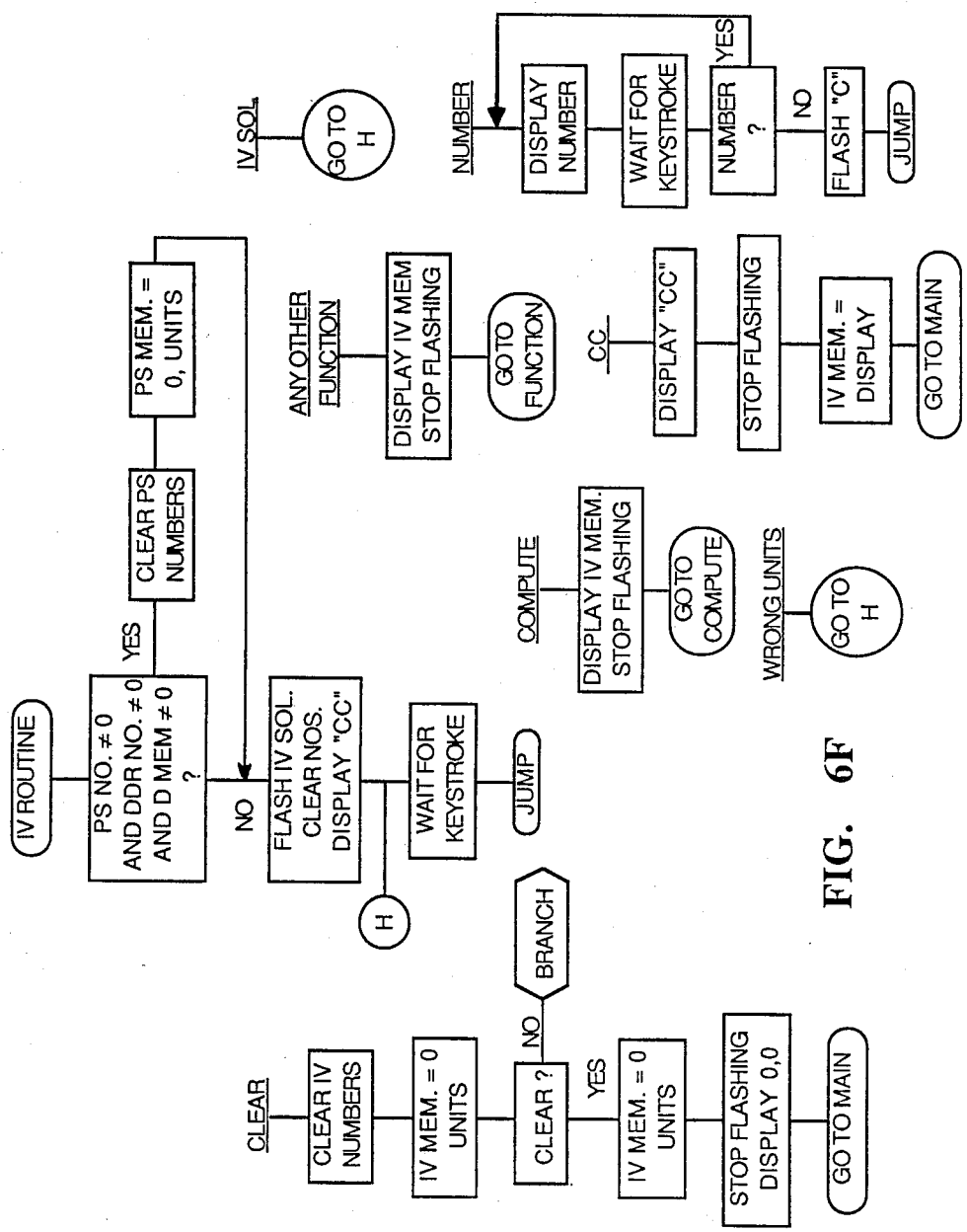
FIG. 6F illustrates the flow chart of the intravenous subroutine of the invention.

Selection of the IV routine from the main sequence causes the microcomputer 130 to execute the sequence shown in FIG. 6F. After a key is depressed, the microcomputer compares the D, DDR and IV SOL numbers to zero. If all these numbers are nonzero, the DDR numbers are cleared from the memory and from the display 114. The light IV SOL is flashed and the "cc" units are displayed. If some of the numbers are not zero, the microcomputer 130 clears the pump setting number before the light IV SOL is flashed and the "cc" units are displayed. The 110 then awaits a keystroke to select one of the clear, compute, any other function, number, wrong units, CC or IV SOL sequences shown in the lower portion of FIG. 6F for execution. The clear, compute and any other function sequences have been previously described.

Depression of the number keys to enter a number for the amount of IV solution causes the number to be displayed and the "C" to flash. The microcomputer 130 then is prepared to jump to the CC sequence.

Depression of the CC key causes the CC segment of the display to light and causes the IV SOL light to stop flashing. The amount of IV solution is displayed and stored before the microcomputer returns to the main sequence.

Depression of the IV SOL key or a key for an incorrect unit causes the microcomputer to go to point H of the IV routine and await a keystroke.

Body Surface Area Routine

Figure 6G:
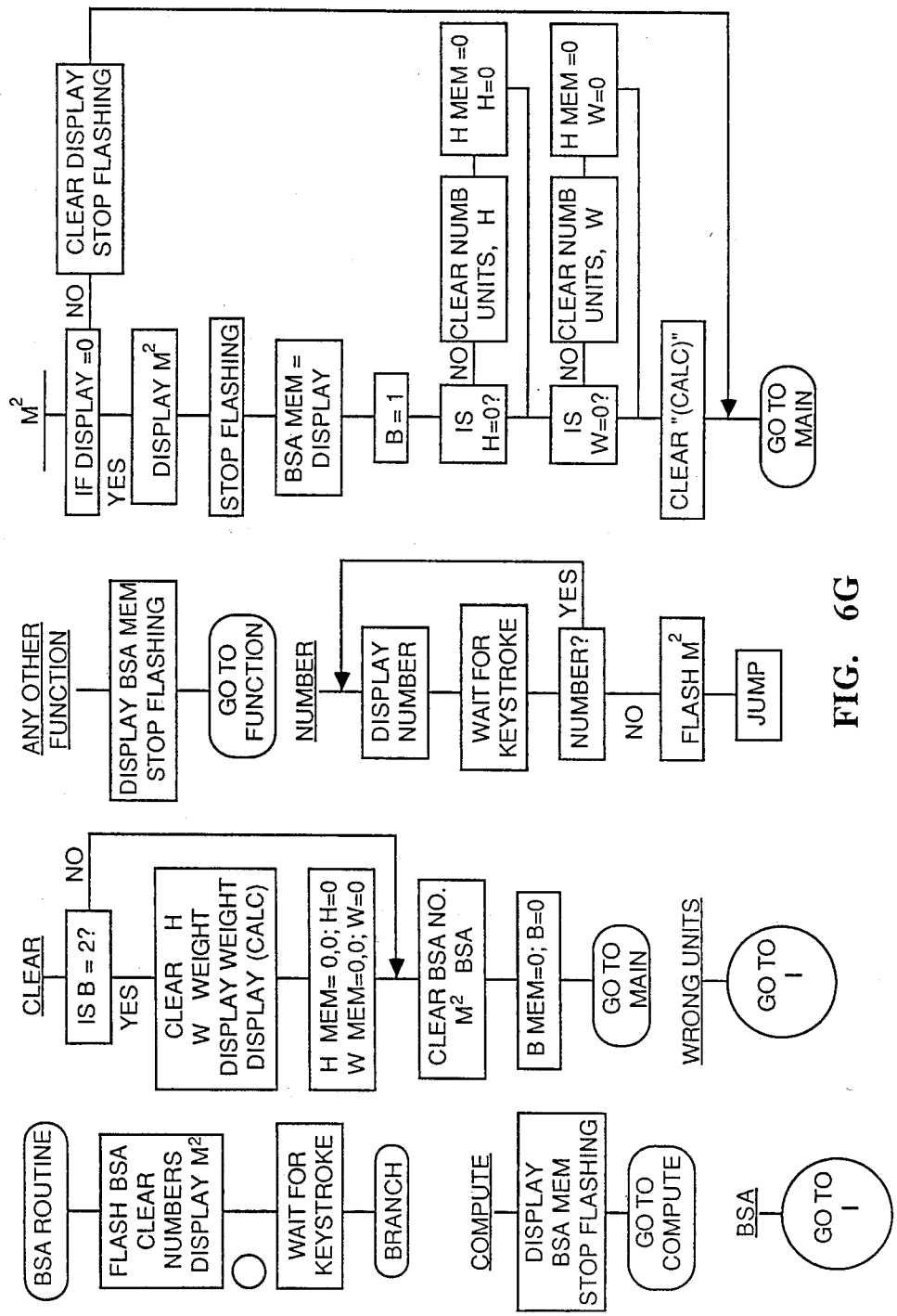
FIG. 6G illustrates the flow chart of the body surface area subroutine of the invention.

If it is necessary to calculate the patient's body surface area (BSA), then the BSA key is depressed to start the body surface area routine of FIG. 6G. The BSA light is flashed, and the display 114 is cleared of numbers. The segment $M^2$ for the units of body surface is displayed, and the 110 awaits a keystroke to select one of the branches for compute, clear, BSA, wrong units, number, $M^2$ or any other function.

If a number key is depressed, the number is displayed, and the units $M^2$ are flashed before the program jumps to the $M^2$ branch. The microcomputer checks to see if the display 114 reads zero. If the display 114 does not read zero, it is cleared before the sequence continues. After ascertaining that the display 114 reads zero, the 110 causes the display to light the segments for $M^2$ and stops flashing the BSA light. The microcomputer then clears the patient's height and weight data and returns to the main sequence.

Weight Routine

Figure 6H:
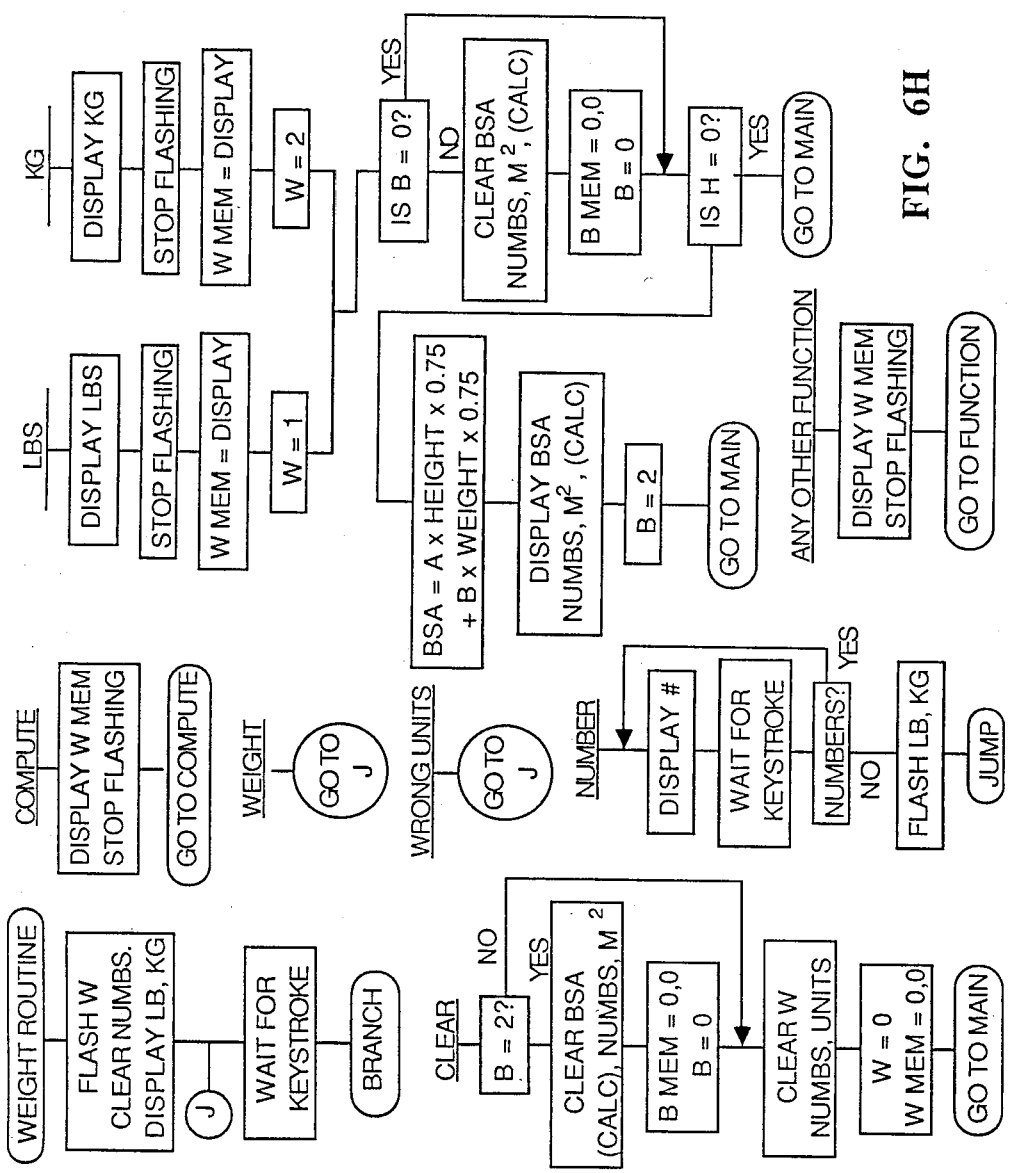
FIG. 6H illustrates the flow chart of the weight subroutine of the invention.
Figure 6I:
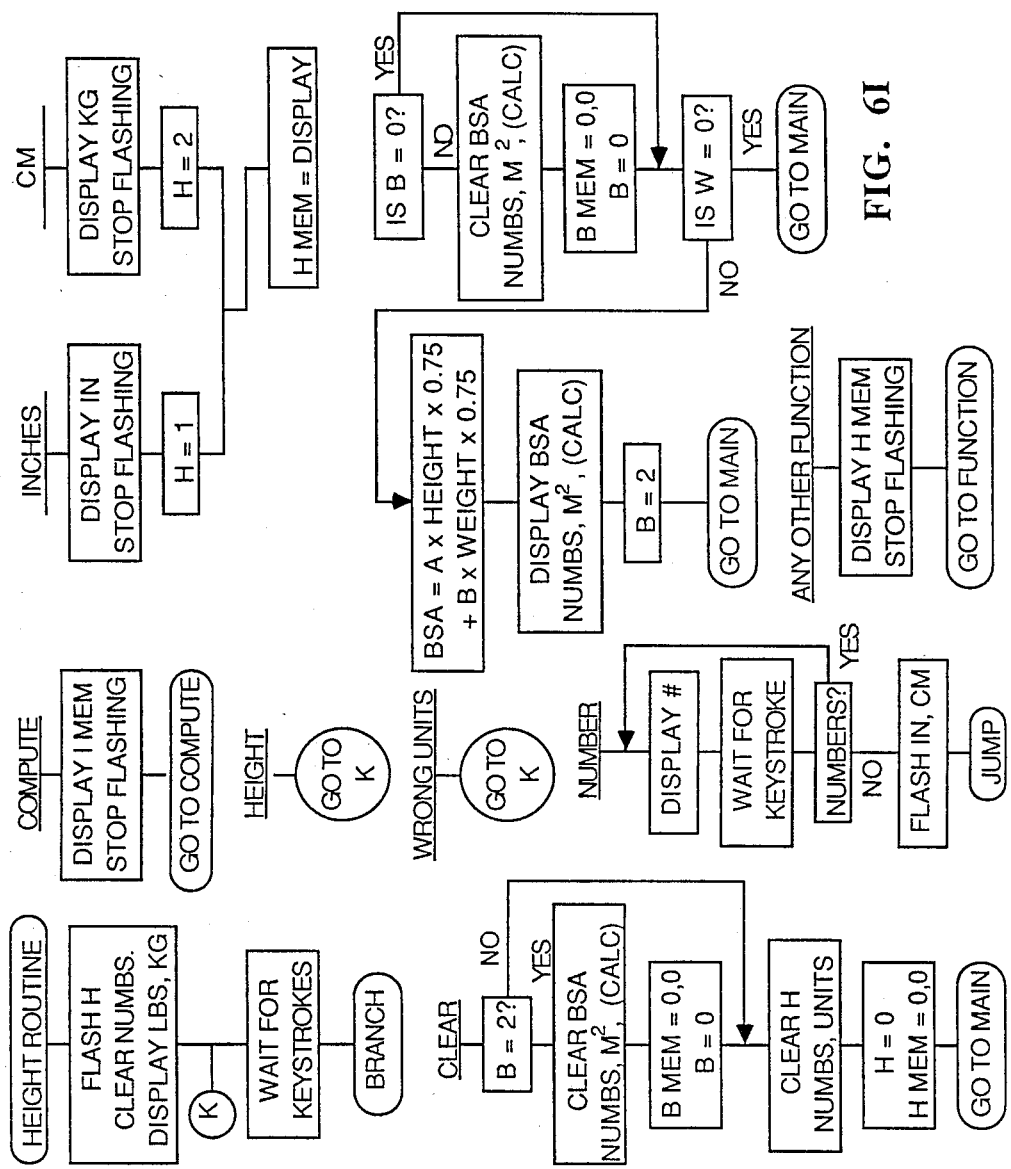
FIG. 6I illustrates the flow chart of the height subroutine of the invention.

If it is necessary to enter the patient's weight, the user depresses the WT key, which causes the microcomputer the execute the sequence shown in FIG. 6H. The WT light is flashed, and the numbers are cleared from the display 114. The units LB and KG are displayed, and the 110 awaits a keystroke indicating which of the compute, clear, weight, number, LB, KG wrong units or any other function branches of FIG. 6H are to be executed.

Depression of the compute, clear or any other function keys causes the execution of steps similar to those described above.

Depression of a number key causes the number to be displayed. After the numbers are entered into the 110, the lights for pounds and kilograms are flashed; and the microcomputer 130 jumps to either the pounds or kilograms sequence of FIG. 6H.

The pounds sequence displays LBS and stops flashing the WT light. The microcomputer 130 compares the body weight area in the memory to zero. If the BSA data is zero and the light is not zero, then the microcomputer 130 computes the BSA as a function of weight and height by a predetermined algorithm. The calculated BSA is displayed, and the microcomputer 130 returns to the main sequence. If the BSA is not zero, the microcomputer 130 clears the previous value and then proceeds to calculate the BSA as described above. If the height is zero, then the microcomputer 130 goes to the main sequence so that the height routine may be executed if the operator desires.

Depression of the weight key or wrong units causes the microcomputer to go to point J of the weight routine to await a keystroke.

Height Routine

If is necessary to enter the patient's height into the 110, the HT key is depressed, which causes the HT light to flash. The units centimeter and inches are displayed, and the 110 awaits a keystroke to indicate which branch of the compute, clear, number, IN, CM, wrong units, height or any other function sequences to execute. The clear, compute and any other function sequences are similar to those described above. Depressing the height key or the wrong units will cause the microcomputer to go to point K of the height routine to await another keystroke.

Depressing the number key causes the number to be displayed. After all of the numbers for the height are entered into the 110, the units IN and CM flash; and the microcomputer jumps to one of the sequences selected by depressing the IN or CM keys. If the IN key is depressed, the display 114 114 stops flashing and the number and units are displayed. The microcomputer checks to see if the BSA is zero. If the BSA is zero, the microcomputer continues to execute steps to calculate the BSA. If the BSA is not zero, then the previous value is cleared so that a new value can be computed. The microcomputer 130 then checks the weight data. If the weight is zero, then the microcomputer goes to the main sequence so that the weight may be entered into the 110 if the operator so desires. If the weight is not zero, then the microcomputer computes the BSA and displays the calculated value in square meters before returning to the main sequence.

Drops Routine

Figure 6J:
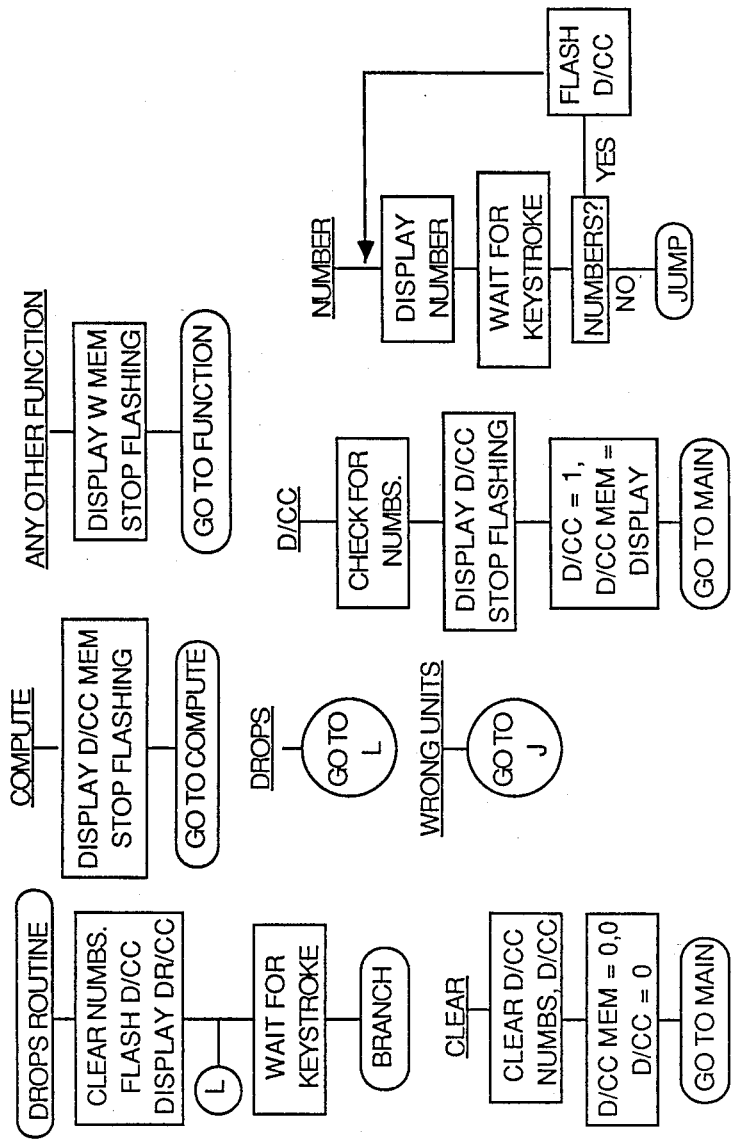
FIG. 6J illustrates the flow chart of the drops subroutine of the invention.
Figure 6:
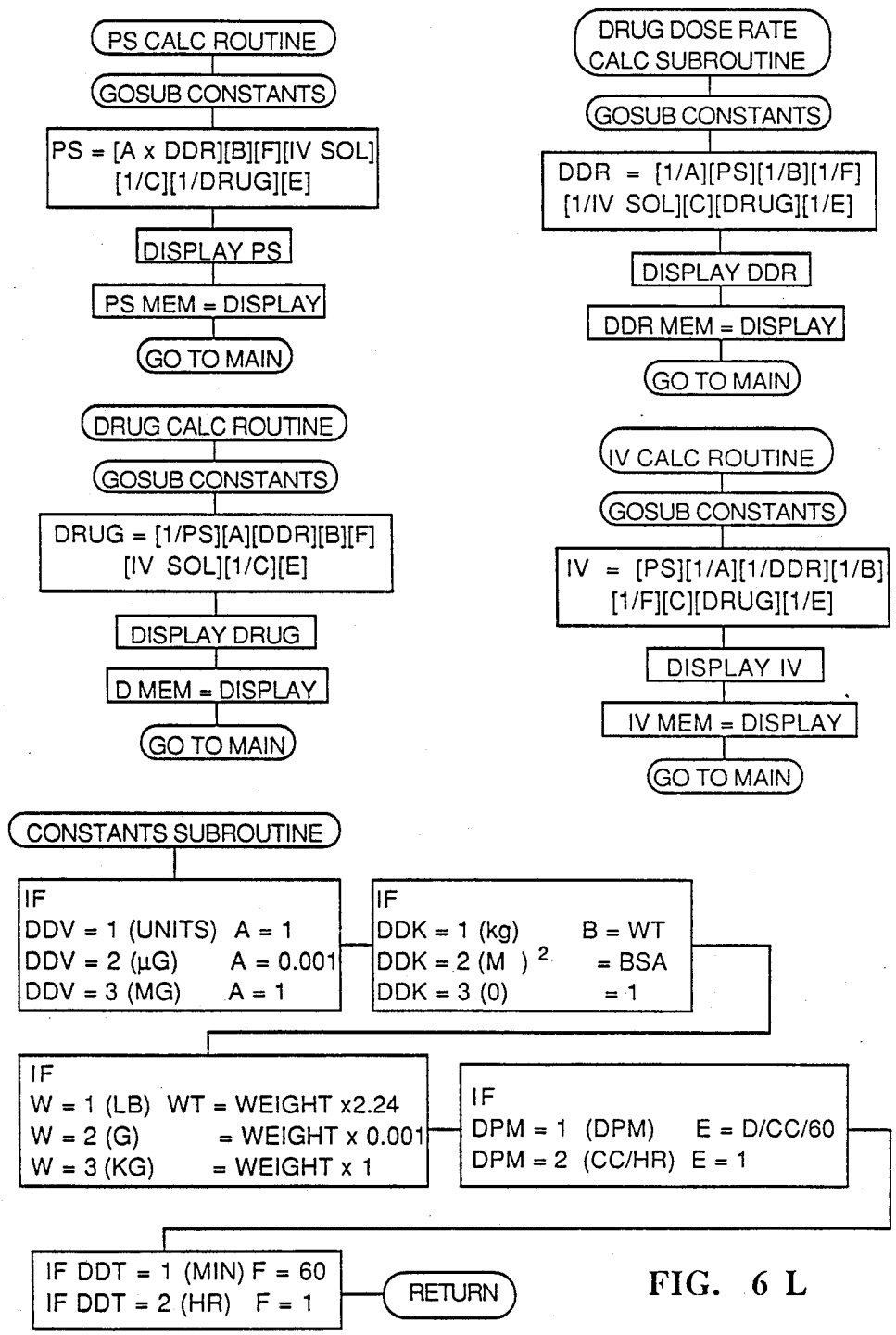
FIG. 6D illustrates the second half of the flow chart of the drug dose rate subroutine of the invention.
FIG. 6K(1) illustrates the first half of the compute routine of the invention.
FIG. 6L illustrates the pump setting, drug dose rate, drug amount, and IV solution calculating subroutines of the invention.

Selection of the drops routine from the main sequence causes the microcomputer to execute the sequence shown in FIG. 6J. The numbers are cleared from the display 114, and the D/CC light is flashed. The system then awaits a keystroke for instructions regarding which of the compute, clear, number, D/CC, drops, wrong units or any other function branches to execute.

The compute, any other function and clear branches function similarly to those previously described. Depression of the keys for drops or incorrect units causes the microcomputer to go to point L of the drops routine.

Depression of a number key causes the number to be displayed. After all of the numbers for the drops have been entered, the microcomputer jumps to the D/CC sequence to calculate the amount of drug per cubic centimeter of IV solution. The first step of the D/CC sequence is to check for numbers. The D/CC segment of the display 114 is lighted, and the drops light stop flashing. The amount of drug per cubic centimeter is stored and displayed before the microcomputer 130 returns to the main sequence.

Compute Routine

Depression of the compute key causes the 110 to execute the sequence of steps shown in FIG. 6K. The flow chart includes several flags to related to the units or status of the variables and functions. These flags are summarized in Table II to facilitate understanding of the compute routine.

TABLE II

Flow Chart Flags

DPM = status of pump setting
　= 0, undefined
　= 1, drops/min
　= 2, cc/hr
DCC = drops/cc status of drops/cc function
　= 0, undefined (implied cc/hr)
　= 1, drops/cc specified
DDU = drug dose rate units
　= 0, undefined
　= 1, UNITS
　= 2, $\mu$g
　= 3, mg
DU = drug unit status
　= 0, undefined
　= 1, UNITS

TABLE II-continued

Flow Chart Flags
　= 2, $\mu$g
　= 3, mg
　= 4, grams
H = height function status
　= 0, not specified
　= 1, inches
　= 2, cm
B = BSA status
　= 0, not specified
　= 1, input
　= 2., computed
W = weight status
　= 0, not specified
　= 1, pounds
　= 2, grams
　= 3, kg
DDK = $M^2$ or kg or blank for DDR
　= 0, undefined
　= 1, kg
　= 2, $M^2$
　= 3, blank
DDT = drug dose rate time
　= 0, undefined
　= 1, hr
　= 2, min The microcomputer 130 first checks the status of the pump setting and the drops setting. If the pump setting is not in drops per minute and the drops/cc are not specified, then the display 114 flashes "ID", displays "PS" and "D" and waits for a keystroke. If the keystroke clears the pump setting or the drug setting, then the flashing ceases. If the keystroke does not clear the pump setting or the drug then the 110 awaits another keystroke that will clear either the pump setting or the drug amount. After the "ID" flashing ceases, the microcomputer executes a branch of the program described subsequently.

If the pump setting is in drops per minute and the drops/cc are specified, then the sequence continues, and the microcomputer determines whether the kilograms of body weight are to be considered in subsequent calculations of the drug dose rate. If the kilograms of body weight are to be considered, then the microcomputer 130 tests to determine whether data for the patient's weight has been entered into the 110. If the weight has not been entered, then "ID" is flashed and the 110 awaits a keystroke to clear the W and DDR settings.

If the weight has been specified, the 110 checks the status of the BSA. If the BSA has not been specified, then "ID" flashes, and DDR and BSA are displayed. The system then awaits a keystroke to clear the DDR, BSA, HT and WT. If the BSA has been input or computed, the microcomputer 130 determines the status of the D/CC. If D/CC=0 then the microcomputer checks the status of the drug units and the weight and height of the patient.

The microcomputer 130 then determines which of the four primary variables is zero while the other three are not zero and calculates the previously unknown variable. The subroutines for calculating the pump setting, the drug dose rate, the drug amount and the amount of IV solution are shown in FIG. 6L. These are standard types of computational subroutines using formulas and constants stored in the memory for calculating the unknown variable.

Although the invention has been described with reference to a specific preferred embodiment, it should be understood that modifications may be made to the preferred embodiment without departing from the spirit of the invention. Accordingly, the invention encompasses the subject matter of the appended claims, which distinctly point out the invention, and equivalents thereof.

What is claimed is:

1. A system for intravenously administering a drug dosage to a patient, the system including a calculation system for calculating an unknown one of the variables in a group including flow control or pump setting, intravenous solution volume, drug dose rate and drug quantity when three of the variables are known for intravenous administration of drugs or the like to a patient, comprising:
   keyboard means for entering data into the system;
   a computation device connected to the keyboard means to receive data for three of the variables therefrom for calculating the unknown variable
   display means connected to the computation device for displaying the data input to the computation device and for displaying a calculated value for the variable that was unknown.

2. The system of claim 1 wherein the keyboard means includes:
   a first set of keys connected to the computation device for listing signal information under the variable headings of variables selected from the pump setting, intravenous solution volume, drug dose rate and drug quantity;
   a second set of keys connected to the computation device for supplying signals thereto indicative of the numerical values of the selected variables; and
   a third set of keys connected to the computation device for supplying signals thereto indicative of the units of the selected variables.

3. The system of claim 2 wherein the third set of keys includes a key for selecting the units of the pump setting to be cubic centimeters per hour.

4. The system of claim 2 wherein the third set of keys includes a key for selecting the units of the pump setting to be drops per minute.

5. The system of claim 2 wherein the third set of keys includes a key for selecting the units of the drug dose rate to be in units of weight per unit time.

6. The system of claim 5 wherein the third set of keys includes a key for selecting the units of the drug dose rate to be in units of weight per unit time per unit area of a patient's body.

7. The system of claim 5 wherein the third set of keys includes a key for selecting the units of the drug dose rate to be in units of weight per unit time per unit weight of a patient's body.

8. The system of claim 2 wherein the third set of keys includes a key for selecting the quantity of drug to be administered to a patient to be in micrograms, milligrams or UNITS.

9. The system of claim 2 wherein the third set of keys includes a key for selecting the quantity of intravenous solution to be administered to a patient to be in cubic centimeters.

10. The system of claim 2 wherein the keyboard further includes a key for supplying data indicative of the patient's body surface area to the computation device.

11. The system of claim 2 wherein the keyboard further includes a key for supplying data indicative of the patient's body weight to the computation device.

12. The system of claim 2 wherein the keyboard further includes a key for supplying data indicative of the patient's body height to the computation device.

13. The system of claim 2 wherein the keyboard further includes a key for providing data indicative of the number of drops of drug solution per minute to be administered to a patient.

14. The system of claim 1 wherein the display means displays permissible units for each selected variable.

15. The system of claim 1 further including display driver means connected between the computing device and the display means for supplying data to the display means.

16. The system of claim 15 wherein the computing device comprises an electronic digital computer and the display means comprises a liquid crystal display device.

17. The system of claim 1 wherein the computation device has an output connected to a valve for controlling the rate at which fluid is administered to the patient.

18. A method for intravenously administering a drug dosage to a patient, the method including determining an unknown one of the variables in the group including fluid flow or pump control setting, intravenous solution volume, drug dose rate and drug quantity when three of the variables are known and one is unknown for intravenous administration of drugs of the like to a patient, comprising the steps of:
   providing a computation device for performing calculations on data input thereto;
   supplying data to the computation device and to identify the names of known variables;
   supplying data indicative of the numerical values of the known variables to the computation device;
   supplying data indicative of the units of the known variables to the computation device;
   supplying data indicative of selected units of the unknown variable to the computation device; and
   computing a numerical value for the previously unknown variable.

19. The method of claim 18 further including the step of providing a display device for displaying permissible units of the variables that may be input to the computation device.

20. The method of claim 18 further including the step of setting at least one of the variables to zero if an attempt is made to enter numerical values for all four variable are input to the computation device.

21. The method of claim 18, further including the step of connecting an output of the computational device to a valve for controlling the rate at which fluid is administered to the patient.

* * * * *